US006617482B1

(12) United States Patent
Venkat et al.

(10) Patent No.: US 6,617,482 B1
(45) Date of Patent: Sep. 9, 2003

(54) REMOVABLE OF POLAR CONTAMINANTS FROM AROMATIC FEEDSTOCKS

(75) Inventors: Chaya Rao Venkat, Sedona, AZ (US); Yun-Yang Huang, Voorhees, NJ (US); Thomas Francis Degnan, Jr., Moorestown, NJ (US); John Paul McWilliams, Swedesboro, NJ (US); Ronald A. Weiss, Flemington, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/639,555

(22) Filed: Aug. 16, 2000

(51) Int. Cl.[7] ............................. C07C 2/66; C07C 7/13
(52) U.S. Cl. .................. 585/448; 585/467; 585/820; 585/823; 585/824
(58) Field of Search .................. 585/448, 467, 585/820, 823, 824

(56) References Cited

U.S. PATENT DOCUMENTS

| 3,293,192 A | | 12/1966 | Maher et al. ................. 252/430 |
| 3,308,069 A | | 3/1967 | Wadlinger et al. ........... 252/455 |
| 3,442,795 A | | 5/1969 | Kerr et al. ................... 208/120 |
| 3,449,070 A | | 6/1969 | McDaniel et al. ............ 23/111 |
| 3,832,449 A | | 8/1974 | Rosinski et al. ............. 423/328 |
| 4,358,362 A | * | 11/1982 | Smith et al. .................. 208/91 |
| 4,439,409 A | | 3/1984 | Puppe et al. ................. 423/328 |
| 4,826,667 A | | 5/1989 | Zones et al. ................. 423/277 |
| 4,891,458 A | | 1/1990 | Innes et al. .................. 585/323 |
| 4,954,325 A | | 9/1990 | Rubin et al. ................. 423/328 |
| 4,992,606 A | | 2/1991 | Kushnerick et al. ......... 585/467 |
| 5,030,786 A | * | 7/1991 | Shamshoum et al. ........ 585/467 |
| 5,236,575 A | | 8/1993 | Bennett et al. ............... 208/46 |
| 5,362,697 A | | 11/1994 | Fung et al. ................... 502/71 |
| 5,536,894 A | * | 7/1996 | Degnan et al. .............. 585/467 |
| 5,744,686 A | | 4/1998 | Gajda .......................... 585/823 |
| 5,942,650 A | | 8/1999 | Gajda .......................... 585/448 |
| 6,297,417 B1 | * | 10/2001 | Samson et al. .............. 585/448 |

FOREIGN PATENT DOCUMENTS

WO    WO98/07673    2/1998

* cited by examiner

*Primary Examiner*—Walter D. Griffin
(74) *Attorney, Agent, or Firm*—Darryl M. Tyus; Linda A. Kubana

(57) ABSTRACT

A process is described for removing polar compounds from an aromatic feedstock which contains polar compounds and which is then used in an alkylation process. The process comprises contacting the feedstock in an adsorption zone at a temperature of less than or equal to 130° C. with an adsorbent selective for the adsorption of said polar compounds and comprising a molecular sieve having pores and/or surface cavities with cross-sectional dimensions greater than 5.6 Angstroms. A treated feedstock substantially free of said polar compounds is withdrawn from the adsorption zone and fed to an alkylation zone for contact under liquid phase alkylation conditions with an alkylating agent in the presence of an alkylation catalyst.

11 Claims, No Drawings

REMOVABLE OF POLAR CONTAMINANTS FROM AROMATIC FEEDSTOCKS

FIELD OF THE INVENTION

This invention relates to a process for removing polar contaminants from aromatic feedstocks and, in particular, to an aromatic alkylation process employing pretreatment of the aromatic feed to remove nitrogen contaminants.

BACKGROUND OF THE INVENTION

In a typical aromatic alkylation process, an aromatic compound is reacted with an alkylating agent, such as an olefin, in the presence of acid catalyst. For example, benzene can be reacted with ethylene or propylene to produce ethylbenzene or cumene, both of which are important intermediates in the chemical industry. In the past, commercial aromatic alkylation processes normally used $AlCl_3$ or $BF_3$ as the acid catalyst, but more recently these materials have been replaced by molecular sieve catalysts. Thus, it is known from U.S. Pat. No. 4,891,458 to employ a zeolite beta catalyst in the alkylation of aromatic compounds with $C_2$ to $C_4$ olefins. In addition, it is known from U.S. Pat. No. 4,992,606 to employ MCM-22 in the alkylation of aromatic compounds with short chain (namely having 1–5 carbon atoms) alkylating agents.

Aromatics alkylation processes employing molecular sieve catalysts can be conducted in either the vapor phase or the liquid phase. However, in view of the improved selectivity and decreased capital and operating costs associated with liquid phase operation, most commercial alkylation processes now operate under at least partial liquid phase conditions. Unfortunately, one disadvantage of operating under liquid phase conditions is that the molecular sieve catalysts tend to be more sensitive to the presence of impurities in the feedstocks, particularly. polar compounds such as nitrogen compounds. Such impurities reduce the acid activity of the catalyst and hence decrease the cycle time between required regenerations of the catalyst.

The use of guard beds to remove trace contaminants from hydrocarbon feed streams is well known in the art. This is especially true for petrochemical and specialty chemical operations where product purity is critical. Normally, materials like bentonite clay, kaolin clay or special activated aluminas are used and are placed upstream of a catalyst-containing reaction vessel. The clay or alumina materials trap impurities in the feedstocks so that product purity specifications can be met and poisoning of the catalyst can be reduced. However, known clay and alumina guard beds have limited ability to reduce the basic nitrogen impurities in aromatic feedstreams to the low levels required for use in liquid phase alkylation processes. Moreover, clays are generally not susceptible to regeneration and hence must be discarded when their adsorption capacity is reached.

U.S. Pat. Nos. 5,744,686 and 5,942,650 describe processes for the removal of nitrogen compounds from an aromatic hydrocarbon stream by contacting the hydrocarbon stream with a selective adsorbent comprising a non-acidic molecular sieve having a silica to alumina molar ratio in excess of 100 and an average diameter less than 5.5 Angstroms. In both cases the selective adsorbent is a molecular sieve selected from the group consisting of pore-closed zeolite 4A, zeolite 4A, silicalite, F-silicalite, ZSM-5, and mixtures thereof.

PCT Publication No. WO 98/07673 discloses a process for preparing an alkylated benzene or mixture of alkylated benzenes in which the benzene feedstock is initially contacted with a solid acid in a pretreatment zone at a temperature greater than about 130° C. and less than about 300° C. The solid acid employed may be an aluminosilicate selected from ZSM-5, ZSM-11, ZSM-35, clinoptilolite, ferrierite, stilbite, EU-1, NU-87, mordenite, zeolite omega, zeolite beta, faujasites, gmelinite, ZSM-12, cancrinite, zeolite L, MCM-22, MCM-41, MCM-49, MCM-56 and MCM-58. The pretreated benzene is then contacted with an alkylating agent in an alkylation zone or with a transalkylating agent in a transalkylation zone in the presence of an alkylation/transalkylation catalyst which may be selected from mordenite, zeolite beta, ZSM-5, ZSM-12, zeolite Y, zeolite omega, EU-1, NU-87, zeolite L, MCM-22, SSZ-25, MCM-36, MCM-49, MCM-56, MCM-58, and a porous crystalline magnesium silicate.

In accordance with the present invention, it has now been found that molecular sieves having pores and/or surface cavities with a cross-sectional size greater than 5.6 Angstroms are more effective for removing nitrogen contaminants from aromatic feedstocks than the small pore materials described in U.S. Pat. Nos. 5,744,686 and 5,942,650. Moreover, it has been found that the removal can be effected at a temperature less than the 130° C. minimum taught in PCT Publication No. WO 98/07673 thereby reducing the formation of by-product hydrocarbon species and hence in potential yield losses, as well as reducing the construction and operating cost of the purification system.

SUMMARY OF THE INVENTION

In one aspect, the invention resides in a process for removing polar compounds from an aromatic feedstock containing polar compounds, said process comprising the steps of:

(a) contacting said feedstock in an adsorption zone with an adsorbent selective for the adsorption of said polar compounds, said adsorbent comprising a molecular sieve having pores and/or surface cavities with cross-sectional dimensions greater than 5.6 Angstroms and said adsorption zone being at a temperature of less than or equal to 130° C.; and (b) withdrawing from said adsorption zone a treated feedstock which is substantially free of said polar compounds.

The term "substantially free of said polar compounds" is used herein to mean that the treated feedstock contains less than 0.1 ppm, and more preferably less than 0.03 ppm, of said polar compounds.

Preferably, the molecular sieve has pores with cross-sectional dimensions greater than 5.6 Angstroms. More preferably, the molecular sieve is selected from the group consisting of zeolite X, zeolite Y, Ultrastable Y (USY), ZSM-12, mordenite, zeolite beta, zeolite L, and zeolite omega.

Alternatively, the molecular sieve has surface cavities with a cross-sectional size greater than 5.6 Angstroms. More preferably, the molecular sieve is selected from the group consisting of MCM-22, MCM-49 and MCM-56.

Preferably, the molecular sieve has a silica to alumina molar ratio less than 100.

Preferably, said temperature is 20 to 125° C. and most preferably is 25 to 110° C.

In a further aspect, the invention comprises an aromatic alkylation process comprising the steps of:

(a) contacting an aromatic feedstock containing polar compounds in an adsorption zone with an adsorbent selective for the adsorption of said polar compounds, said adsorbent comprising a molecular sieve having pores and/or surface cavities with a cross-sectional dimensions greater than 5.6 Angstroms and said adsorption zone being at a temperature of less than or equal to 130°;

(b) withdrawing from said adsorption zone a treated feedstock which is substantially free of said polar compounds; and (c) passing said treated feedstock to an alkylation zone containing an alkylation catalyst comprising a molecular sieve and contacting said treated feedstock with an alkylating agent in said alkylation zone under liquid phase alkylation conditions so as to produce an alkylated aromatic compound.

Preferably, the alkylation catalyst comprises a molecular sieve selected from the group consisting of zeolite beta, MCM-22, MCM-49 and MCM-56.

DETAILED DESCRIPTION OF THE INVENTION

This invention relates to a process for removing polar contaminants from an aromatic feedstock. More particularly, this invention relates to a liquid phase aromatics alkylation process which includes subjecting the aromatic feedstock to a pretreatement step for the selective removal of polar contaminants that poison aromatic alkylation catalysts. Such contaminants include nitrogen, sulfur, and oxygen containing compounds, particularly those that boil in the same ranges as benzene, toluene or xylenes. Especially problematic are basic nitrogen compounds, such as pyridine, quinoline, N-formyl-morpholine and N-methyl-pyrrolidone, because they neutralize the solid acids that comprise most present day aromatic alkylation catalysts. The process may also effective for the removal of inorganic cations, particularly salts. For example, depending on the molecular sieve adsorbent employed, the selective sorption process envisioned here may also be able to remove alkali metal cations (Na, K, etc.) and alkaline earth cations (Ca, Mg, etc.) that are problematic in acid catalysis.

The term "aromatic" in reference to the feedstocks which can be treated by the adsorption process of the present invention is used herein in accordance with its art-recognized scope which includes alkyl substituted and unsubstituted mono- and polynuclear compounds.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable unsubstituted aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, and pentadecytoluene. Very often alkylate is obtained as a high boiling fraction in which the alkyl group attached to the aromatic nucleus varies in size from about $C_6$ to about $C_{12}$.

Reformate containing substantial quantities of benzene, toluene and/or xylene constitutes a particularly useful feed for the alkylation process of this invention.

Typical feedstocks for use in the process of the invention include benzene, toluene, xylenes and mixtures thereof, with benzene being particularly preferred. As used in commercial alkylation processes, such aromatic feedstocks typically contain from about 0.1 to about 10 ppm, and more typically from about 0.5 to about 3 ppm of polar impurities. In addition, the feedstocks may contain water up to saturation conditions.

The selective sorption process of the invention comprises passing the aromatic feedstock containing polar compounds to an adsorption zone containing an adsorbent selective for the adsorption of said polar compounds, wherein the adsorbent comprises a molecular sieve having pores and/or surface cavities with a cross-sectional dimensions greater than 5.6 Angstroms and the temperature in the adsorption zone is maintained below 130° C., and then withdrawing a treated feedstock which is substantially free of said polar compounds from the adsorption zone.

In one embodiment, the molecular sieve used as the adsorbent is a molecular sieve having pores which have average cross-sectional dimensions greater than 5.6 Angstroms. Examples of suitable large pore molecular sieves include zeolite X, zeolite Y, dealuminized zeolite Y, Ultrastable Y (USY), ZSM-12, mordenite, zeolite beta, zeolite L, and zeolite omega. Dealuminized zeolite Y (Deal Y) may be prepared by the method found in U.S. Pat. No. 3,442,795. Low sodium Ultrastable Y (USY) is described in U.S. Pat. Nos. 3,293,192 and 3,449,070. ZSM-12 is described in U.S. Pat. No. 3,832,449. Zeolite beta is described in U.S. Pat. No. 3,308,069. A preferred adsorbent is zeolite 13X, which is the sodium form of zeolite X.

In an alternative embodiment, the molecular sieve used as the adsorbent is a molecular sieve having surface cavities with a cross-sectional size greater than 5.6 Angstroms. In this case, the pores of the molecular sieve may have cross-sectional dimensions greater, less than or equal to 5.6 Angstroms. Examples of molecular sieves having such surface cavities are MCM-22 (described in U.S. Pat. No. 4,954,325), PSH-3 (described in U.S. Pat. No. 4,439,409), SSZ-25 (described in U.S. Pat. No. 4,826,667), MCM-49 (described in U.S. Pat. No. 5,236,575), and MCM-56 (described in U.S. Pat. No. 5,362,697).

The molecular sieve used as the adsorbent in the process of the invention is preferably based on an acidic molecular sieve having a framework silica-to-alumina molar ratio less than 100 and more preferably greater than 10, for example 20 to 50. Higher silica zeolites have been found to be more effective when water is present. However, the higher silica materials also have fewer sites for adsorption and are therefore less effective where the aromatic feedstock is completely free of water.

The molecular sieve used in the adsorption zone of the process of the invention will typically be in the form particles, for example extrudate, spheres or pellets, which contain the molecular sieve together with a binder system to improve physical integrity. The binder system can be any of a number of amorphous metal oxides including alumina, silica, zirconia, and titania, with alumina being preferred.

It is important that the temperature in the adsorption zone is maintained at or below 130° C. since operating at higher temperatures is found to increase the formation of by-product hydrocarbon species and hence increase potential yield losses. Moreover, operating the adsorption system at higher temperatures increases the construction and operating cost of the system. Preferably, the temperature in the adsorption zone is 20 to 125° C. and most preferably is 25 to 110° C. Other conditions in the adsorption zone are not critical but generally include a pressure of atmospheric pressure to 1000 psig, and a WHSV of 0.5 to 400 WHSV. The aromatic effluent withdrawn from the adsorption zone is substantially free of polar impurities and typically contains less than 0.1 ppm, and preferably less than 0.03 ppm, of polar impurities.

The adsorption zone is normally in the form of a fixed bed in which the aromatic feed stream passes either upflow or downflow through the bed.

In operation, the molecular sieve adsorbent removes polar impurities from the aromatic feedstock until its sorption capacity is reached. At this stage, the adsorbent must be regenerated either by stripping with a desorbent, such as steam or nitrogen, or by heating the adsorbent in air to burn off the sorbed material. In order to allow continuous treatment of the aromatic feedstock, the adsorption zone may include a plurality of beds of molecular sieve adsorbent so that, as one bed is being regenerated, other bed(s) are available for service.

Where the adsorption step of the present invention is used as a pretreatment for an aromatic feedstock used in an aromatic alkylation process, the adsorption zone is positioned upstream of the aromatic alkylation reactor and effectively protects the alkylation catalyst from polar poisons in the feedstock. The aromatic feedstock is treated in the absence of olefins. Any olefin feed to the alkylation reactor is introduced downstream of the adsorption zone so that no reaction can occur between the aromatic feed stream and any olefins, aside from trace olefins that may be present in the aromatic feed as trace contaminants. In any case, the amount of alkylated aromatics produced by reaction in the adsorption zone is less than 1 wt % of the aromatic feed stream and more typically is less than 0.1 wt % of the aromatic feed stream.

After passage through the adsorption zone, the treated aromatic feedstock is fed to an aromatic alkylation reactor containing an aromatic alkylation catalyst where the feedstock is contacted under liquid phase conditions with an alkylating agent.

The alkylating agents useful in the process of this invention generally include any aliphatic or aromatic organic compound having one or more available alkylating aliphatic groups capable of reaction with the aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols and trialcohols) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides.

Mixtures of light olefins are also useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

The alkylating agents useful in the alkylation process of this invention are preferably olefins having 2 to 5 carbon atoms and most preferably ethylene or propylene. Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes. The preferred reaction products are ethylbenzene and cumene.

The aromatic alkylation catalyst is a molecular sieve and preferably is a molecular sieve selected from zeolite beta, MCM-22, MCM-49 and MCM-56. The same molecular sieve can be used in the alkylation reactor as that used for the adsorption zone.

The alkylation step of this invention is conveniently conducted under conditions including a temperature of 0° to 500° C., and preferably 50° to 250° C., a pressure of 0.2 to 250 atmospheres, and preferably 5 to 100 atmospheres, a molar ratio of alkylatable aromatic compound to alkylating agent of 0.1:1 to 50:1, and preferably 0.5:1 to 10:1, and a feed weight hourly space velocity (WHSV) of 0.1 to 500 hr$^{-}$, preferably 0.5 to 100 hr$^{-1}$.

When benzene is alkylated with ethylene to produce ethylbenzene, the alkylation reaction is preferably carried out under conditions including a temperature between 300° and 600° F. (150° and 316° C.), preferably between 400° and 500° F. (205° and 260° C.), a pressure up to 3000 psig (20875 kPa), preferably between 400 and 800 psig (2860 and 5600 kPa), a space velocity between 0.1 and 20 WHSV, preferably between 1 and 6 WHSV, based on the ethylene feed, and a ratio of the benzene to the ethylene in the alkylation reactor from 1:1 to 30:1 molar, preferably from 1:1 to 10:1 molar.

When benzene is alkylated with propylene to produce cumene, the reaction is preferably carried out under conditions including a temperature of up to 250° C., e.g., up to 150° C., e.g., from 10° to 125° C.; a pressure of 250 atmospheres or less, e.g., from 1 to 30 atmospheres; and an aromatic hydrocarbon weight hourly space velocity (WHSV) of from 5 hr$^{-1}$ to 250 hr$^{-1}$, preferably from 5 hr$^{-1}$ to 50 hr$^-$.

The aromatic compound reacts with the alkylating agent in the alkylation reactor to produce to the desired monoalkylated aromatic product, for example ethylbenzene or cumene. However, the alkylation product stream will inevitably contain polyalkylated species which are preferably separated and fed to a transalkylation zone for reaction with additional alkylatable aromatic compound, such as benzene, in the presence of a transalkylation catalyst. The transalkylation catalyst is preferably selected from zeolite beta, TEA-mordenite, MCM-22, MCM-49 and MCM-56. The transalkylation reaction is also preferably conducted under liquid phase conditions.

The invention will now be more particularly described with reference to the following examples.

EXAMPLE 1

Comparative

A mixture of 1 part by weight acetonitrile in 99 parts by weight toluene was prepared using reagent grade toluene and acetonitrile. A series of batch runs was carried out with ZSM-5 zeolite having a silica-to-alumina molar ratio of 26 as the adsorbent. Prior to contact with the acetonitrile:toluene mixture, the ZSM-5 was activated by calcination at 500° C. In each run, a fixed volume of the toluene:acetonitrile solution was contacted with varying amounts of dry adsorbent in a glass container at 25° C. and atmospheric pressure. After 12 hours gas chromatographic analysis of the solution was carried out, with 2 wt % 2,3 dimethylbutane being added to the solution as an internal reference. The results of the experiments are given in Table 1 below:

TABLE 1

Adsorption of Acetonitrile by ZSM-5 ($SiO_2/Al_2O_3$ = 26:1)

| Solution Charge, ml | Adsorbent Charge, g | Equilibrium Acetonitrile Concentration, wt % | Acetonitrile Adsorbed, mg/gram of adsorbent |
|---|---|---|---|
| 10 | 3.6 | 0.029 | 22.7 |
| 10 | 3.15 | 0.033 | 25.8 |
| 10 | 1.84 | 0.146 | 39.0 |
| 10 | 1.60 | 0.201 | 41.9 |
| 10 | 1.20 | 0.336 | 46.2 |
| 10 | 0.54 | 0.645 | 54.4 |

At equilibrium, the uptake of acetonitrile by the ZSM-5 adsorbent was approximately 55 mg/g of adsorbent.

EXAMPLE 2

Comparative

A mixture of 1 part by weight acetonitrile in 99 parts by weight toluene was prepared using reagent grade toluene and acetonitrile. A series of batch runs was carried out with another sample of ZSM-5 zeolite that had a silica-to-alumina molar ratio of 700. Prior to contact with the acetonitrile:toluene mixture, the ZSM-5 was activated by calcination at 500° C. In the same manner as in Example 1, a fixed volume of the toluene:acetonitrile solution was contacted with varying amounts of dry adsorbent in a glass container at 25° C. and atmospheric pressure. After 12 hours gas chromatographic analysis of the solution was carried out, with 2 wt % 2,3 dimethylbutane being added to the solution as an internal reference. The results of the experiments are given in Table 2 below:

TABLE 2

Adsorption of Acetonitrile by ZSM-5 ($SiO_2/Al_2O_3$ = 700:1)

| Solution Charge, ml | Adsorbent Charge, g | Equilibrium Acetonitrile Concentration, wt % | Acetonitrile Adsorbed, Mg/gram of adsorbent |
|---|---|---|---|
| 10 | 4.20 | 0.092 | 18.2 |
| 10 | 3.88 | 0.072 | 20.1 |
| 10 | 2.05 | 0.235 | 31.1 |
| 10 | 1.65 | 0.271 | 36.8 |
| 10 | 1.43 | 0.325 | 39.3 |
| 10 | 0.71 | 0.577 | 48.9 |

At equilibrium, the uptake of acetonitrile by the ZSM-5 ($SiO_2/Al_2O_3$=700:1) adsorbent was approximately 49 mg/g of adsorbent, which is slightly lower than the value obtained in Example 1.

EXAMPLE 3

A mixture of 1 part by weight acetonitrile in 99 parts by weight toluene was prepared using reagent grade toluene and acetonitrile. A series of batch runs was carried out with a sample of MCM-22 zeolite that had a silica-to-alumina ratio of 26:1. Prior to contact with the acetonitrile:toluene mixture, the MCM-22 was activated by calcination at 500° C. In the same manner as in Example 1, a fixed volume of the toluene:acetonitrile solution.was contacted with varying amounts of dry adsorbent in a glass container at 25° C. and atmospheric pressure. After 12 hours gas chromatographic analysis of the solution was carried out, with 2 wt % 2,3 dimethylbutane being added to the solution as an internal reference. The results of the experiments are given in Table 3 below:

TABLE 3

Adsorption of Acetonitrile by MCM-22 ($SiO_2/Al_2O_3$ = 26:1)

| Solution Charge, ml | Adsorbent Charge, g | Equilibrium Acetonitrile Concentration, wt % | Acetonitrile Adsorbed, mg/gram of adsorbent |
|---|---|---|---|
| 10 | 4.48 | 0.000 | 18.7 |
| 10 | 3.90 | 0.000 | 21.6 |
| 10 | 2.80 | 0.012 | 29.6 |
| 10 | 2.14 | 0.048 | 37.6 |
| 10 | 1.32 | 0.203 | 50.6 |
| 10 | 0.76 | 0.454 | 59.4 |
| 10 | 0.71 | 0.484 | 60.0 |

At equilibrium, the uptake of acetonitrile by the MCM-22 ($SiO_2/Al_2O_3$=26:1) adsorbent was approximately 60 mg/g of adsorbent, which is higher than that obtained in either Example 1 or 2. In addition, the MCM-22 adsorbent was more effective in removing acetonitrile from solutions at the higher loadings of acetonitrile. Complete removal of acetonitrile was achieved.

EXAMPLE 4

A mixture of 1 part by weight acetonitrile in 99 parts by weight toluene was prepared using reagent grade toluene and acetonitrile. A series of batch runs was carried out with a sample of 13X zeolite that had a silica-to-alumina ratio of 2.5:1 and which had been activated by calcination at 500° C. In the same manner as in Example 1, a fixed volume of the toluene:acetonitrile solution was contacted with varying amounts of dry adsorbent in a glass container at 25° C. and atmospheric pressure. After 12 hours gas chromatographic analysis of the solution was carried out, with 2 wt % 2,3 dimethylbutane being added to the solution as an internal reference. The results of the experiments are given in Table 4, below:

TABLE 4

Adsorption of Acetonitrile by 13X ($SiO_2/Al_2O_3$ = 2.5:1)

| Solution Charge, ml | Adsorbent Charge, g | Equilibrium Acetonitrile Concentration, wt % | Acetonitrile Adsorbed, mg/gram of adsorbent |
|---|---|---|---|
| 10 | 5.83 | 0.004 | 14.4 |
| 10 | 3.72 | 0.007 | 22.5 |
| 10 | 2.23 | 0.014 | 37.2 |
| 10 | 1.68 | 0.030 | 48.5 |
| 10 | 0.74 | 0.085 | 103.7 |

At equilibrium, the uptake of acetonitrile by the 13X adsorbent was at least 103 mg/g of adsorbent, which is higher than that obtained in either Example 1, 2, or 3.

example 5

A solution was prepared containing 25 ppm of N-formyl-morpholine and 200 ppm water and was contacted with various molecular sieve adsorbents under a nitrogen atmosphere and at reflux conditions of about 110° C. After 24 hours the amount of nitrogen remaining in the solution and the amount of nitrogen adsorbed by the adsorbent. were measured by chemiluminescence. The results are shown in Table 5.

TABLE 5

| Adsorbent | Mass of Adsorbent | "N" in Solution | "N" in Adsorbent |
|---|---|---|---|
| USY | | | |
| 250 mL solution | 0.02 | 24 | 9750 |
| 50 mL solution | 0.1 | 1.3 | 5500 |
| 50 mL solution | 1 | 1 | 859 |
| 50 mL solution | 5 | 1 | 331 |
| 13X | | | |
| 250 mL solution | 0.02 | 24 | 9500 |
| 50 mL solution | 0.1 | 7.6 | 6200 |
| 50 mL solution | 1 | 1 | 215 |
| 50 mL solution | 5 | 1 | 180 |
| Spent MCM-22 | | | |
| 250 mL solution | 0.02 | 28 | 3500 |
| 50 mL solution | 0.1 | 20 | 1800 |
| 50 mL solution | 1 | 1 | 1200 |
| 50 mL solution | 5 | 1 | 148 |

The spent MCM-22 was a catalyst which had been used in a commercial cumene plant and which had been regenerated after removal from the plant at the end of its useful life.

Whereas each sieve tested showed activity for the removal of the N-formyl-morpholine, the USY and 13X exhibited higher sorption capacity than spent MCM-22.

What is claimed is:

1. An aromatic alkylation process comprising:
   (a) contacting an aromatic feedstock containing polar compounds in an adsorption zone with an adsorbent selective for the adsorption of said polar compounds, said adsorbent comprising a molecular sieve selected from MCM-22, MCM49, MCM-56, zeolite X, zeolite Y, Ultrastable Y (USY), mordenite, zeolite beta, zeolite L, or zeolite omega and said adsorption zone being at a temperature of less than or equal to 125° C.;
   (b) withdrawing from said adsorption zone a treated feedstock which is substantially free of said polar compounds; and
   (c) passing said treated feedstock to an alkylation zone containing an alkylation catalyst and contacting said treated feedstock with an alkylating agent in said alkylation zone under alkylation conditions so as to produce an alkylated aromatic compound.

2. The process of claim 1, wherein the molecular sieve is selected from the group consisting of zeolite X, zeolite Y and Ultrastable Y (USY).

3. The process of claim 1, wherein the molecular sieve has a silica to alumina molar ratio less than 100.

4. The process of claim 1, wherein said temperature is 20 to 125° C.

5. The process of claim 1, wherein said temperature is 25 to 110° C.

6. The process of claim 1, wherein the alkylation catalyst comprises a molecular sieve selected from the group consisting of zeolite beta, MCM-22, MCM-49 and MCM-56.

7. The process of claim 1, wherein the aromatic feedstock is benzene and alkylating agent is ethylene or propylene.

8. An aromatic alkylation process comprising:
   (a) contacting an aromatic feedstock containing polar compounds in an adsorption zone with an adsorbent selective for the adsorption of said polar compounds, said adsorbent comprising a molecular sieve selected from zeolite X, zeolite Y, or Ultrastable Y (USY), and said adsorption zone being at a temperature of less than or equal to 125° C.;
   (b) withdrawing from said adsorption zone a treated feedstock which is substantially free of said polar compounds; and
   (c) passing said treated feedstock to an alkylation zone containing an alkylation catalyst comprising a molecular sieve and contacting said treated feedstock with an alkylating agent in said alkylation zone under liquid phase alkylation conditions so as to produce an alkylated aromatic compound.

9. The process of claim 8, wherein the alkylation catalyst comprises a molecular sieve selected from the group consisting of zeolite beta, MCM-22, MCM-49 and MCM-56.

10. The process of claim 8, wherein the aromatic feedstock is benzene and alkylating agent is ethylene or propylene.

11. An aromatic alkylation process comprising:
    (a) contacting an aromatic feedstock containing polar compounds in an adsorption zone with an adsorbent selective for the adsorption of said polar compounds, said adsorbent comprising a molecular sieve selected from MCM-22, MCM49, MCM-56, zeolite X, zeolite Y, Ultrastable Y (USY), mordenite, zeolite beta, zeolite L, or zeolite omega and said adsorption zone being at a temperature of less than or equal to 125° C.;
    (b) withdrawing from said adsorption zone a treated feedstock which contains less than 0.1 ppm of said polar compounds; and
    (c) passing said treated feedstock to an alkylation zone containing an alkylation catalyst and contacting said treated feedstock with an alkylating agent in said alkylation zone under alkylation conditions so as to produce an alkylated aromatic compound.

* * * * *